US008389550B2

(12) United States Patent
Buettelmann et al.

(10) Patent No.: US 8,389,550 B2
(45) Date of Patent: Mar. 5, 2013

(54) ISOXAZOLES / O-PYRIDINES WITH ETHYL AND ETHENYL LINKER

(75) Inventors: Bernd Buettelmann, Schopfheim (DE); Matthew C. Lucas, Verona, NJ (US); Andrew Thomas, Binningen (CH)

(73) Assignees: Hoffmann-La Roche Inc., Nutley, NJ (US); Roche Palo Alto LLC, Palo Alto, CA (US)

( * ) Notice: Subject to any disclaimer, the term of this patent is extended or adjusted under 35 U.S.C. 154(b) by 180 days.

(21) Appl. No.: 12/706,722

(22) Filed: Feb. 17, 2010

(65) Prior Publication Data
US 2010/0216845 A1 Aug. 26, 2010

(30) Foreign Application Priority Data
Feb. 25, 2009 (EP) .................................. 09153575

(51) Int. Cl.
*A61K 31/4439* (2006.01)
*C07D 413/06* (2006.01)
(52) U.S. Cl. ..................... 514/340; 546/272.1
(58) Field of Classification Search ............... 546/272.1; 514/340
See application file for complete search history.

(56) References Cited

U.S. PATENT DOCUMENTS

| 4,639,266 A | 1/1987 | Heubach et al. |
| 2003/0055085 A1 | 3/2003 | Wagener et al. |
| 2004/0006226 A1 | 1/2004 | Ladduwahetty et al. |

FOREIGN PATENT DOCUMENTS

| DE | 3525205 | 3/1986 |
| GB | 2336589 | 10/1999 |
| JP | 2007230909 | 9/2007 |
| WO | 0129015 | 4/2001 |
| WO | 0134603 | 5/2001 |
| WO | 0250062 | 6/2002 |
| WO | 02/081474 | 10/2002 |
| WO | 03/004027 | 1/2003 |
| WO | 03015771 | 2/2003 |
| WO | 03044017 | 5/2003 |
| WO | 2004048349 | 6/2004 |
| WO | 2005014553 | 2/2005 |
| WO | 2005118568 | 12/2005 |
| WO | 2005123672 | 12/2005 |
| WO | 2006044617 | 4/2006 |
| WO | 2006069155 | 6/2006 |
| WO | 2007009275 | 1/2007 |
| WO | 2007039389 | 4/2007 |
| WO | 2007052843 | 5/2007 |
| WO | 2007/137954 | 6/2007 |
| WO | 2007076260 | 7/2007 |
| WO | 2007092751 | 8/2007 |
| WO | 2008025539 | 3/2008 |
| WO | 2008025540 | 3/2008 |
| WO | 2006037480 | 4/2010 |

OTHER PUBLICATIONS

Kumar, et al., Tetrahedron Letters, vol. 47, (2006), p. 1457-1460.
Burke, et al., Journal of Natural Products, 1986, vol. 49, pp. 522-523.
Hormi, Organic Syntheses, vol. 8, p. 247 (1993) & vol. 66, (1988), p. 173.
Andosova et al., Pharmaceutical Chemistry Journal (English Translation), vol. 12, No. 8, 1978, pp. 1019-1022.
Doyle, et al., Journal of the Chem. Society, 1963, pp. 5838-5845.
Anderson, et al., Journal of Organic Chem. vol. 51(6), 1986, pp. 945-947.
Bourbeau et al., Organic Letters, vol. 8(17), 2006, pp. 3670-3680.
Waldo et al., Org. Lett. vol. (7) pp. 5203-5205 (2005).
Seydel et al., J. Med. Chem. vol. (19) pp. 483-492 (1976).
Kirk, K. L., J. Org. Chem. vol. (43) pp. 4381-4383 (1978).
Ley et al., Angew Chem, 2003 vol. 115 p. 5558-5606.
Hüttel et al., Liebigs, Ann. Chem. vol. 593, pp. 200-207 (1955) (English language translation attached).
Austin et al., J. Org. Chem. vol. 46, pp. 2280-2286 (1981).
Schlosser et al., Eur. J. Org. Chem. vol. (24), p. 4181-4184 (2002).
Félix et al., J. Org. Chem. 1995, vol. 60 p. 3907-3909.
Otani et al., Neuroscience Letters, 2005, vol. 381, pp. 108-113.
Papadimitriou et al., Neuropsychobiology, 2001, vol. 43(3) pp. 141-144.
McCauley et al., Amer. J. Med. Genetics, 2004, 131B, pp. 51-59.
DeLong et al., Autism, 2007, vol. 11(2) pp. 135-147.
Solis-Anez et al., Investigacion Clinica, 2007, vol. 48, pp. 529-541 (English language Abstract Attached).
Fernandez et al., Nature Neurosci. 2007, vol. 10, pp. 411-413.
Rueda et al., Neuroscience Letters, 2008, vol. 433, pp. 22-27.
Cui et al., Cell, 2008, vol. 135, pp. 549-560.
McNamara et al., Psychobiology (1993), vol. 21, pp. 101-108.
Goodman et al., Tetrahedron (1999) vol. 55 pp. 15067-15070.
Roy et al., Synthesis, 2003 pp. 1347-1356.
White, et al., Journal of Organic Chemistry (1981), vol. 46(11) pp. 2273-2280.
Shi Shun et al., J. Org. Chem. vol. 68 (2003) pp. 6810-6813.
Lam et al., Bioorganic & Medicinal Chemistry Letters (2003) vol. 13(10) pp. 1795-1799.
Wang et al., Journal of Fluorine Chemistry, vol. 111(2) pp. 241-246 (2001).
Hamper et al., J. Agric. Food Chem. (1995), vol. 43, pp. 219-228.
Translation of Korean Off Act in Corres Korean Appl 20117019615 Dec. 20, 2012.

*Primary Examiner* — Patricia Morris
(74) *Attorney, Agent, or Firm* — George W. Johnston; Patricia S. Rocha-Tramaloni; Kimberly J. Prior

(57) ABSTRACT

The present invention is concerned with novel isoxazole-pyridines of formula I

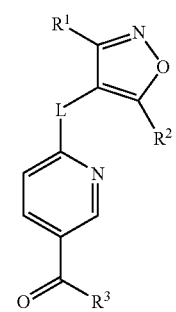

wherein $R^1$, $R^2$, $R^3$ and L are as described herein, as well as pharmaceutically acceptable salts and esters thereof. The active compounds of the present invention have affinity and selectivity for GABA A α5 receptor. Further the present invention is concerned with the manufacture of the active compounds of formula I, pharmaceutical compositions containing them and their use as pharmaceutical agents.

18 Claims, No Drawings

ISOXAZOLES / O-PYRIDINES WITH ETHYL AND ETHENYL LINKER

PRIORITY TO RELATED APPLICATION(S)

This application claims the benefit of European Patent Application No. 09153575.7, filed Feb. 25, 2009, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in Psychobiology, 1993, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

Literature has been published to establish the link between GABA A α5 subunits and the treatment of various diseases of the Central Nervous System, like Neuroscience Letts., 2005, 381, 108-13, Neuropsychobiology, 2001, 43(3), 141-44, Amer. J. Med. Genetics, 2004, 131B, 51-9, Autism 2007, 11(2): 135-47, Investigacion Clinica, 2007, 48, 529-41, Nature Neuroscience, 2007, 10, 411-13, Neuroscience Letts., 2008, 433, 22-7 and Cell 2008, 135, 549-60.

SUMMARY OF THE INVENTION

The present invention provides isoxazole-pyridines having affinity and selectivity for GABA A α5 receptor, their manufacture, pharmaceutical compositions containing them and their use as pharmaceuticals.

In particular, the present invention provides isoxazole-pyridines of formula I

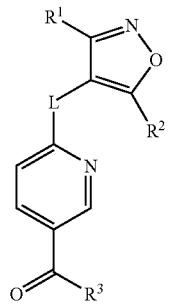

wherein
L is —$CH_2$—$CH_2$— or —CH=CH—;
$R^1$ is lower-alkyl or aryl, wherein lower-alkyl is optionally substituted with 1-4 substituents independently selected from the group consisting of fluoro, cyano, hydroxy, lower-alkoxy and fluoro-lower-alkoxy, and wherein aryl is optionally substituted with 1-4 substituents independently selected from the group consisting of halogen, cyano, hydroxy, lower-alkyl, fluoro-lower-alkyl, cyano-lower-alkyl, hydroxy-lower-alkyl, lower-alkyl-C(O)OH, lower-alkyl-C(O)O-lower-alkyl, lower-alkyl-CO—$NH_2$, lower-alkyl-CO—N(H, lower-alkyl), lower-alkyl-CO—N(lower-alkyl)$_2$, lower-alkyl-N(H, lower-alkyl), lower-alkyl-N(lower-alkyl)$_2$, lower-alkoxy-lower-alkyl, CO-lower-alkyl, COOH, COO-lower-alkyl, $CONH_2$, CON(H, lower-alkyl), CON(lower-alkyl)$_2$, $NH_2$, N(H, lower-alkyl), N(lower-alkyl)$_2$, lower-alkoxy, fluoro-lower-alkoxy, $SO_2$-lower-alkyl, $SO_2$—$NH_2$, $SO_2$—N(H, lower-alkyl), $SO_2$—N(lower-alkyl)$_2$, cycloalkyl, phenyloxy and phenyl;
$R^2$ is lower-alkyl optionally substituted with 1-4 substituents independently selected from the group consisting of fluoro, cyano, hydroxy, lower-alkoxy and fluoro-lower-alkoxy;
$R^3$ is —O—$R^4$ or N($R^5$,$R^6$);
$R^4$ is hydrogen or lower-alkyl;
$R^5$ is hydrogen or lower-alkyl; and
$R^6$ is lower-alkyl, hydroxy-lower-alkyl or heterocyclyl, or wherein $R^5$ and $R^6$ are bound together and with the Nitrogen atom to which they are attached form a heterocyclyl;
or a pharmaceutically acceptable salt or ester thereof.

The compounds of present invention are preferably inverse agonists of GABA A α5.

The present invention provides compounds of formula I per se and their pharmaceutically acceptable salts and esters, pharmaceutical compositions containing them, the preparation of the above-mentioned compounds and compositions, and the use of the above-mentioned compounds in the treatment or prevention of diseases related to the GABA A α5 receptor.

The compounds of present invention and their pharmaceutically acceptable salts and esters can be used, alone or in combination with other drugs, as cognitive enhancers or for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders.

DETAILED DESCRIPTION OF THE INVENTION

The following definitions of the general terms used in the present description apply irrespective of whether the terms in question appear alone or in combination.

The term "substituted", unless specifically defined otherwise, means that the specified group or moiety can bear 1, 2, 3, 4, 5 or 6 substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents. 1, 2, 3, 4 or 5 substituents are preferred, unless specifically defined otherwise. Particularly preferred are 1, 2, 3 or 4 substituents.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

As used herein, the term "lower-alkyl" denotes a saturated straight- or branched-chain group containing from 1 to 7 carbon atoms, for example, methyl, ethyl, propyl, isopropyl, n-butyl, isobutyl, sec-butyl, tent-butyl and the like. Preferred lower-alkyl groups are n-butyl, isopropyl and methyl.

The term "hydroxy-lower-alkyl" denotes a lower-alkyl group as defined above wherein at least one of the hydrogen atoms of the alkyl group is replaced by a hydroxy group. Examples of hydroxy-lower-alkyl include but are not limited to methyl, ethyl, propyl, isopropyl, isobutyl, sec-butyl, tert-butyl, pentyl or n-hexyl substituted by one or more hydroxy group(s), in particular with one, two or three hydroxy groups, preferably with one or two hydroxy group, as well as those groups specifically illustrated by the examples herein below. Among the preferred hydroxy-lower-alkyl groups are 2-hydroxy-ethyl, 2-hydroxy-1-methyl-ethyl, 2-hydroxy-1-hydroxymethyl-ethyl, and 2-hydroxy-2-methyl-propyl.

The term "cyano-lower-alkyl" denotes a lower-alkyl group as defined above wherein at least one of the hydrogen atoms of the alkyl group is replaced by a cyano group. Examples of cyano-lower-alkyl include but are not limited to methyl, ethyl, propyl, isopropyl, isobutyl, sec-butyl, tert-butyl, pentyl or n-hexyl substituted by one or more cyano group(s), preferably by one, two or three, and more preferably by one cyano group, as well as those groups specifically illustrated by the examples herein below. Examples of cyano-lower-alkyl groups are e.g. $C(CN)H_2$, $C(CN)_2H$, $C(CN)H_2CH_2$, $C(CN)H_2(CH_2)_2$ and $(C(CN)H_2)_2CH$.

The term "fluoro-lower-alkyl" refers to lower-alkyl groups which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H—CF_2$.

The term "halogen" refers to fluorine, chlorine, bromine, and iodine.

The term "lower-alkoxy" denotes a group —O—R wherein R is lower-alkyl as defined above.

The term "fluoro-lower-alkoxy" refers to the group —O—R', wherein R' is fluoro-lower-alkyl as defined above. Examples of fluoro-lower-alkoxy groups are e.g. $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "cycloalkyl" refers to a monovalent saturated cyclic hydrocarbon radical of 3 to 7 ring carbon atoms, preferably 3 to 6 carbon atoms, such as cyclopropyl, cyclobutyl, cyclopentyl, or cyclohexyl.

The term "heterocyclyl" refers to a monovalent 3 to 7 membered saturated monocyclic ring containing one, two or three ring heteroatoms selected from N, O and S. One or two ring heteroatoms are preferred. Preferred are 4 to 6 membered heterocyclyl or 5 to 6 membered heterocyclyl, each containing one or two ring heteroatoms selected from N, O and S. Examples for heterocyclyl moieties are tetrahydro-furanyl, tetrahydro-pyranyl, pyrrolidinyl, morpholinyl, thiomorpholinyl, piperidinyl, or piperazinyl. Among the preferred heterocyclyls are tetrahydro-furan-3-yl, and tetrahydro-pyran-4-yl. Heterocyclyl can optionally be substituted as described for aryl.

The term "aryl" refers to a monovalent aromatic carbocyclic ring system, preferably to phenyl or naphthyl, and more preferably to phenyl. Aryl can optionally be substituted as described herein.

Compounds of formula I can form pharmaceutically acceptable acid addition salts. Examples of such pharmaceutically acceptable salts are salts of compounds of formula I with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula I which comprise an acidic group, such as e.g. a COOH group, can further form salts with bases. Examples of such salts are alkaline, earth-alkaline and ammonium salts such as e.g. Na-, K-, Ca- and trimethylammoniumsalt. The term "pharmaceutically acceptable salts" also refers to such salts.

The term "pharmaceutically acceptable esters" embraces derivatives of the compounds of formula I, in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aryl-lower-alkyl esters are examples of suitable esters. The methyl, ethyl, propyl, butyl and benzyl esters are preferred esters. The term "pharmaceutically acceptable esters" furthermore embraces compounds of formula I in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

"Therapeutically effective amount" means an amount that is effective to prevent, alleviate or ameliorate symptoms of disease or prolong the survival of the subject being treated.

In detail, the present invention provides compounds of formula I

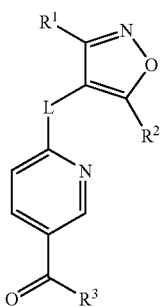

wherein
L is —CH₂—CH₂— or —CH═CH—;
R¹ is lower-alkyl or aryl,
wherein lower-alkyl is optionally substituted with 1-4 substituents independently selected from the group consisting of fluoro, cyano, hydroxy, lower-alkoxy and fluoro-lower-alkoxy;
and wherein aryl is optionally substituted with 1-4 substituents independently selected from the group consisting of halogen, cyano, hydroxy, lower-alkyl, fluoro-lower-alkyl, cyano-lower-alkyl, hydroxy-lower-alkyl, lower-alkyl-C(O)OH, lower-alkyl-C(O)O-lower-alkyl, lower-alkyl-CO—NH₂, lower-alkyl-CO—N(H, lower-alkyl), lower-alkyl-CO—N(lower-alkyl)₂, lower-alkyl-N(H, lower-alkyl), lower-alkyl-N(lower-alkyl)₂, lower-alkoxy-lower-alkyl, CO-lower-alkyl, COOH, COO-lower-alkyl, CONH₂, CON(H, lower-alkyl), CON(lower-alkyl)₂, NH₂, N(H, lower-alkyl), N(lower-alkyl)₂, lower-alkoxy, fluoro-lower-alkoxy, SO₂-lower-alkyl, SO₂—NH₂, SO₂—N(H, lower-alkyl), SO₂—N(lower-alkyl)₂, cycloalkyl, phenyloxy and phenyl;
R² is lower-alkyl optionally substituted with 1-4 substituents independently selected from the group consisting of fluoro, cyano, hydroxy, lower-alkoxy and fluoro-lower-alkoxy;
R³ is —O—R⁴ or N(R⁵,R⁶);
R⁴ is hydrogen or lower-alkyl;
R⁵ is hydrogen or lower-alkyl; and
R⁶ is lower-alkyl, hydroxy-lower-alkyl or heterocyclyl,
or wherein R⁵ and R⁶ are bound together and with the Nitrogen atom to which they are attached form a heterocyclyl;
and pharmaceutically acceptable salts and esters thereof.

Compounds of formula I are individually preferred and pharmaceutically acceptable salts thereof are individually preferred and pharmaceutically acceptable esters thereof are individually preferred, with the compounds of formula I being particularly preferred.

The compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemate, by asymmetric synthesis or asymmetric chromatography (chromatography with a chiral adsorbents or eluant). The invention embraces all of these forms.

Further, it is to be understood that every embodiment relating to a specific residue R¹ to R⁶ as disclosed herein can be combined with any other embodiment relating to another residue R¹ to R⁶ as disclosed herein.

In certain embodiments of the compound of formula I, L is preferably —CH═CH—.

In certain embodiments of the compound of formula I, R¹ is aryl or lower-alkyl, preferably lower-alkyl. Even more preferred compounds of the present invention are those wherein R¹ is n-butyl.

In certain embodiments of the compound of formula I, R² is lower-alkyl, preferably methyl.

In certain embodiments of the compound of formula I, R³ is preferably NR⁵R⁶.

In certain embodiments of the compound of formula I, R⁴ is preferably hydrogen or methyl.

In certain embodiments of the compound of formula I, R⁵ is preferably hydrogen.

In certain embodiments of the compound of formula I, R⁶ is lower-alkyl, hydroxy-lower-alkyl or heterocyclyl, preferably hydroxy-lower-alkyl or heterocyclyl. Even more preferred compounds of the present invention are those wherein R⁶ is 2-hydroxy-1-methyl-ethyl or tetrahydro-furan-3-yl.

In particular, preferred compounds are the compounds of formula I described in the examples as individual compounds as well as pharmaceutically acceptable salts and pharmaceutically acceptable esters thereof. Furthermore, the substituents as found in the specific examples described below, individually constitute separate preferred embodiments of the present invention.

Particularly preferred compounds of formula I of present invention are those selected from the group consisting of:
6-[(E)-2-(5-Methyl-3-phenyl-isoxazol-4-yl)-vinyl]-nicotinic acid methyl ester,
N-Isopropyl-6-[(E)-2-(5-methyl-3-phenyl-isoxazol-4-yl)-vinyl]-nicotinamide,
6-[(E)-2-(5-Methyl-3-phenyl-isoxazol-4-yl)-vinyl]-N-(tetrahydro-pyran-4-yl)-nicotinamide,
N-(2-Hydroxy-ethyl)-6-[(E)-2-(5-methyl-3-phenyl-isoxazol-4-yl)-vinyl]-nicotinamide,
N-(2-Hydroxy-1-methyl-ethyl)-6-[(E)-2-(5-methyl-3-phenyl-isoxazol-4-yl)-vinyl]-nicotinamide,
6-[(E)-2-(5-Methyl-3-phenyl-isoxazol-4-yl)-vinyl]-nicotinic acid,
6-[(E)-2-(3-Butyl-5-methyl-isoxazol-4-yl)-vinyl]-nicotinic acid methyl ester,
6-[(E)-2-(3-Butyl-5-methyl-isoxazol-4-yl)-vinyl]-N-isopropyl-nicotinamide,
6-[(E)-2-(3-Butyl-5-methyl-isoxazol-4-yl)-vinyl]-N-(tetrahydro-furan-3-yl)-nicotinamide,
6-[(E)-2-(3-Butyl-5-methyl-isoxazol-4-yl)-vinyl]-N-(2-hydroxy-1-methyl-ethyl)-nicotinamide,
6-[(E)-2-(3-Butyl-5-methyl-isoxazol-4-yl)-vinyl]-N-(2-hydroxy-2-methyl-propyl)-nicotinamide,
6-[(E)-2-(3-Butyl-5-methyl-isoxazol-4-yl)-vinyl]-N-(tetrahydro-pyran-4-yl)-nicotinamide,
6-[(E)-2-(3-Butyl-5-methyl-isoxazol-4-yl)-vinyl]-N—((R)-2-hydroxy-1-methyl-ethyl)-nicotinamide,
6-[(E)-2-(3-Butyl-5-methyl-isoxazol-4-yl)-vinyl]-N—((S)-2-hydroxy-1-methyl-ethyl)-nicotinamide
6-[(E)-2-(3-Butyl-5-methyl-isoxazol-4-yl)-vinyl]-N-(2-hydroxy-1-hydroxymethyl-ethyl)-nicotinamide,
N-Isopropyl-6-[2-(5-methyl-3-phenyl-isoxazol-4-yl)-ethyl]-nicotinamide,
6-[2-(3-Butyl-5-methyl-isoxazol-4-yl)-ethyl]-N-(2-hydroxy-1-methyl-ethyl)-nicotinamide, and
6-[2-(3-Butyl-5-methyl-isoxazol-4-yl)-ethyl]-N-(tetrahydro-furan-3-yl)-nicotinamide,
and pharmaceutically acceptable salts and esters thereof.

Even more preferred compounds of formula I of present invention are those selected from the group consisting of:
6-[(E)-2-(3-Butyl-5-methyl-isoxazol-4-yl)-vinyl]-N-(tetrahydro-furan-3-yl)-nicotinamide, and
6-[(E)-2-(3-Butyl-5-methyl-isoxazol-4-yl)-vinyl]-N-(2-hydroxy-1-methyl-ethyl)-nicotinamide,
and pharmaceutically acceptable salts and esters thereof.

The compounds of formula IA and IB, encompassed by compounds of formula I, and their pharmaceutically acceptable salts and esters can be prepared by a process comprising the steps of:

a) reacting a compound of formula II:

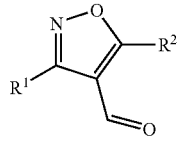

with a compound of formula III:

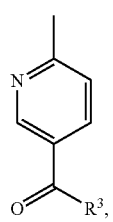

to give a compound of formula IA:

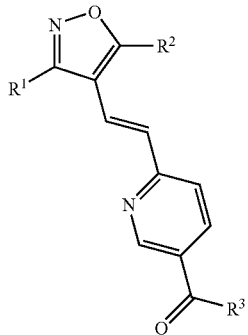

or
b) reacting a compound of formula IV:

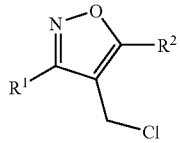

with a compound of formula III:

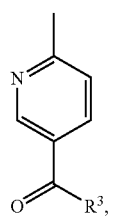

to give a compound of formula IB:

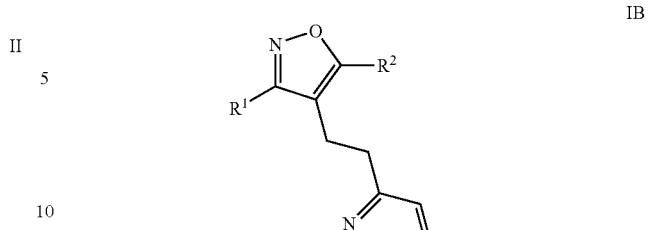

or
c) hydrogenation of a compound of formula IA:

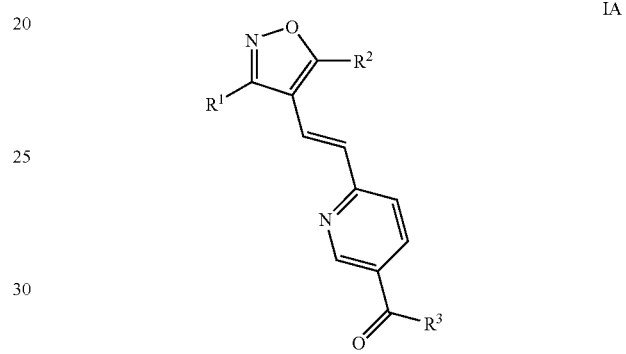

to give a compound of formula IB:

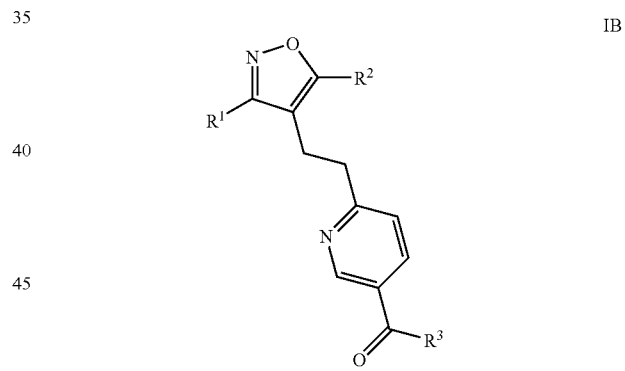

wherein $R^1$, $R^2$ and $R^3$ are as defined above.

The reaction of a compound of formula II with a compound of formula III can be carried out under conditions as described in the examples or under conditions well known to the person skilled in the art. For example, the reaction can be performed in the presence of a solvent/reagent, like acetic anhydride, and acetic acid at elevated temperatures e.g. at 100 to 200° C.

The reaction of a compound of formula IV with a compound of formula V can be carried out under conditions as described in the examples or under conditions well known to the person skilled in the art. For example, the reaction can be performed in a suitable solvent, like THF, in the presence of a base, like butyllithium, at reduced temperatures like −80 to −40° C.

The present invention also relates to compounds of formula I as defined above, when prepared by a process as described above.

The present compounds of formula I and their pharmaceutically acceptable salts and esters can be prepared by a process comprising the steps of:

a) reacting a compound of formula 1

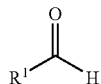

1 with hydroxylamine hydrochloride in a suitable solvent, such as ethanol and water, in the presence of a base, such as aqueous sodium hydroxide, to give a compound of formula 2:

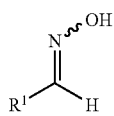

2 b) reacting the compound of formula 2 with a chlorinating agent, such as N-chlorosuccinimide, in a suitable solvent, such as DMF, to give a compound of formula 3:

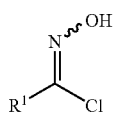

3 c) and then reacting the compound of formula 3 with a compound of formula 4:

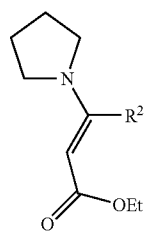

4 to give a compound of formula 5:

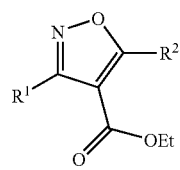

5 d) reacting a compound of formula 5 with a hydrolytic agent, such as NaOH or LiOH, in a suitable solvent, such as THF, MeOH or EtOH, water, to give a compound of formula 6:

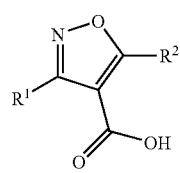

6 followed by reacting a compound of formula 6 with a reducing agent, such as lithiumaluminiumhydride or ethylchloroformate, in the presence of sodiumborohydride in a suitable solvent, such as THF or water, to give a compound of formula 7:

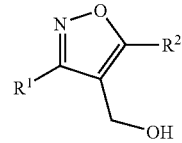

7 e) reacting a compound of formula 7 with an oxidizing agent, such as manganese dioxide or PCC, in a suitable solvent, such as dichloromethane, to give a compound of formula II:

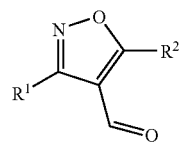

II f) reacting a compound of formula 7 with thionyl chloride in a suitable solvent, such as dichloromethane, to give a compound of formula IV:

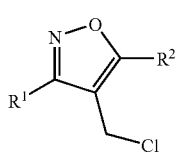

IV g) reacting a compound of formula 8 with a compound of formula II in the presence of a solvent/reagent, such as acetic anhydride, and acetic acid at elevated temperatures such as 120° C.

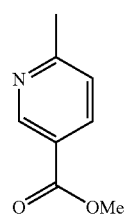

8 to give a compound of formula IA-1:

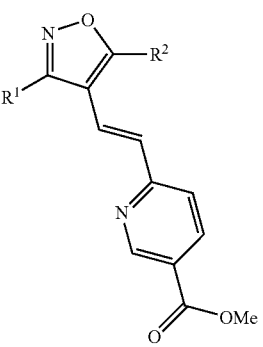

IA-1 h) reacting a compound of formula 9 with a base, such as butyllithium, at reduced temperatures, such as <−68° C., in a suitable solvent, such as THF, with a compound of formula IV:

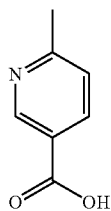

to give a compound of formula IB-1

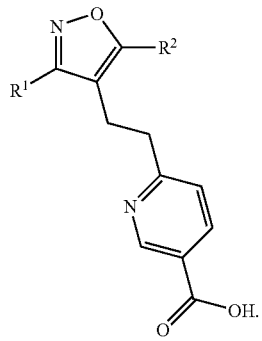

In accordance with Scheme 1, compounds of formula I can be prepared following standard methods.

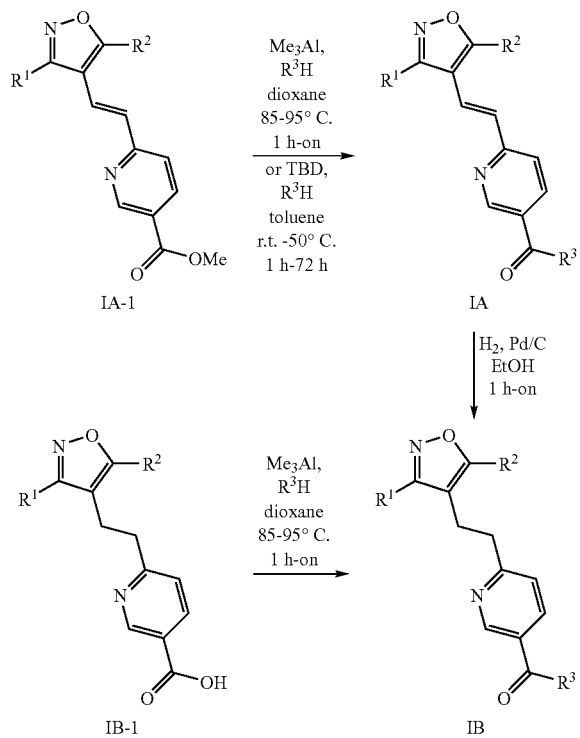

on = overnight
rt = room temperature
DMF = N,N-dimethylformamide
DCM = dichloromethane
TBD = 1,5,7-Triazabicyclo[4.4.0]dec-5-ene
PCC = pyridinium chlorochromate The corresponding salts with acids can be obtained by standard methods known to the person skilled in the art, e.g. by dissolving the compound of formula I in a suitable solvent, such as e.g. dioxan or THF, and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt, such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization.

The conversion of compounds of formula I into pharmaceutically acceptable esters can be carried out e.g. by treatment of a suitable carboxy group present in the molecule with a suitable alcohol using e.g. a condensing reagent such as benzotriazol-1-yloxytris(dimethylamino) phosphonium hexafluorophosphate (BOP), N,N-dicyclohexylcarbodiimide (DCC), N-(3-dimethyl aminopropyl)-N'-ethylcarbodiimide hydrochloride (EDCI) or O-(1,2-dihydro-2-oxo-1-pyridyl)-N,N,N,N-tetra-methyluronium-tetrafluoroborate (TPTU), or by direct reaction with a suitable alcohol under acidic conditions, as for example in the presence of a strong mineral acid like hydrochloric acid, sulfuric acid and the like. Compounds having a hydroxyl group can be converted to esters with suitable acids by analogous methods.

Insofar as their preparation is not described in the examples, the compounds of formula I as well as all intermediate products can be prepared according to analogous methods or according to the methods set forth above. Starting materials are commercially available, known in the art or can be prepared by methods known in the art or in analogy thereto.

It will be appreciated that the compounds of general formula I in this invention can be derivatized at functional groups to provide derivatives which are capable of conversion back to the parent compound in vivo.

As described above, the novel compounds of the present invention and their pharmaceutically acceptable salts and esters possess valuable pharmacological properties and have been found to be ligands for GABA A α5 receptors. The compounds of the present invention can therefore be used, either alone or in combination with other drugs, for the treatment or prevention of diseases which are modulated by ligands for GABA A receptors containing the α5 subunit. These diseases include, but are not limited to acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke, attentional disorders and need for cognition enhancement.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

In another preferred embodiment, the invention relates to a method for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for cognition enhancement, which method comprises administering a compound as defined above to a human being or animal.

The invention also embraces the use of compounds as defined above for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for cognition enhancement.

The invention also relates to the use of compounds as described above for the preparation of medicaments for the treatment or prevention of diseases which are related to the GABA A α5 receptor, particularly for the treatment or prevention of acute and/or chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for the preparation of cognitive enhancers. Such medicaments comprise a compound as described above.

The treatment or prevention of cognitive disorders, Alzheimer's disease, schizophrenia, positive, negative and/or cognitive symptoms associated with schizophrenia, Down syndrome, and neurofibromatosis type I, is preferred.

Particularly preferred is the treatment or prevention of Alzheimer's disease.

Particularly preferred is the treatment or prevention of Down syndrome.

Particularly preferred is the treatment or prevention of neurofibromatosis type I.

The compounds were investigated in accordance with the test given hereinafter:

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM CaCl$_2$, 1.2 mM MgCl$_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [3H]flumazenil at a concentration of 1 nM for α1, α2, α3 subunits and 0.5 nM for α5 subunits and the test compound in the range of $10\text{-}10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and the preferred compounds were found to possess a Ki value for displacement of [$^3$H]flumazenil from α5 subunits of the rat GABA A receptor of 100 nM or less. Most preferred are compounds with a Ki (nM)<35. In a preferred embodiment the compounds of the invention are binding selective for the α5 subunit relative to the α1, α2 and α3 subunit.

Representative test results, obtained by the above described assay measuring binding affinity to HEK293 cells expressing human (h) receptors, are shown in table 1 below:

TABLE 1

Binding affinities to HEK293 cells expressing human (h) receptors of representative examples.

| Example | hKi GABA A α5 nM |
|---|---|
| 1 | 13.9 |
| 2 | 5.0 |
| 3 | 6.0 |
| 4 | 2.0 |
| 5 | 2.9 |
| 6 | 38.6 |
| 7 | 8.1 |
| 8 | 18.6 |
| 9 | 8.9 |
| 10 | 8.2 |
| 11 | 16.3 |
| 12 | 12.9 |
| 13 | 12.2 |
| 14 | 14.1 |
| 15 | 5.3 |
| 16 | 57.6 |
| 17 | 49.4 |
| 18 | 58.6 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 0.1 to 1000 mg per person of a compound of general formula I should be appropriate, although the above upper limit can also be exceeded when necessary.

The following examples illustrate the present invention without limiting it. All temperatures are given in degrees Celsius.

Example A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

Example C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples 1-18 are provided for illustration of the invention. They should not be considered as limiting the scope of the invention, but merely as being representative thereof.

Example 1

6-[(E)-2-(5-Methyl-3-phenyl-isoxazol-4-yl)-vinyl] nicotinic acid methyl ester

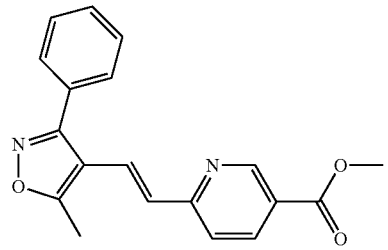 [SMILES: COC(=O)c1ccc(/C=C/c2c(-c3ccccc3)noc2C)nc1]

a) 5-Methyl-3-phenyl-isoxazole-4-carbaldehyde

To a solution of (5-methyl-3-phenyl-4-isoxazolyl)methanol (8.0 g, 42 mmol) in dichloromethane (1 L) was added manganese(IV) oxide (81.7 g, 0.85 mol) and the resulting mixture stirred vigorously for 7 days. The mixture was then filtered and the filtrate evaporated to afford the title compound (7.1 g, 89%) as a light yellow solid. MS: m/e=188.2 [M+H]$^+$.

b) 6-[(E)-2-(5-Methyl-3-phenyl-isoxazol-4-yl)-vinyl]-nicotinic acid methyl ester To a solution of methyl 6-methylnicotinate (800 mg, 5.29 mmol) in acetic anhydride (2.5 mL) and acetic acid (0.5 mL) was added 5-methyl-3-phenyl-4-isoxazolecarbaldehyde (1.0 g, 5.34 mmol) and the reaction mixture warmed to 120° C. After 8 days at this temperature, the reaction mixture was cooled to room temperature then diluted with water and extracted with ethyl acetate. The combined organic extracts were washed with saturated aqueous sodium bicarbonate solution, then dried, filtered and concentrated. Purification by chromatography (silica, heptane:ethyl acetate=100:0 to 1:1) to give the title compound (920 mg, 54%) as an off white solid. MS: m/e=321.0 [M+H]$^+$.

Example 2

N-Isopropyl-6-[(E)-2-(5-methyl-3-phenyl-isoxazol-4-yl)-vinyl]-nicotinamide

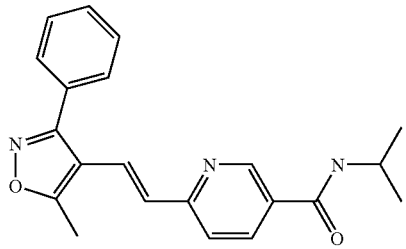 [SMILES: Cc1onc(-c2ccccc2)c1/C=C/c1ccc(C(=O)NC(C)C)cn1]

A solution of trimethylaluminium (2 M in toluene, 1.25 mL, 2.0 mmol) was added dropwise (exothermic) to a solution of isopropylamine (210 µL, 2.0 mmol) in dioxane (6 mL) and the resulting mixture was stirred at room temperature for 1 h. Then 6-[(E)-2-(5-methyl-3-phenyl-isoxazol-4-yl)-vinyl]-nicotinic acid methyl ester (200 mg, 0.62 mmol) was added. The resulting mixture was then heated at 90° C. for 2 h and then cooled to room temperature and then poured into water and extracted with ethyl acetate which was then washed with brine, dried over sodium sulfate and evaporated. Purification by chromatography (SiO$_2$, heptane:ethyl acetate=100:0 to 1:4) afforded the title compound (170 mg, 78%) which was obtained as a white solid after trituration from diisopropylether/ethyl acetate. MS: m/e=348.3 [M+H]$^+$.

Example 3

6-[(E)-2-(5-Methyl-3-phenyl-isoxazol-4-yl)-vinyl]-N-(tetrahydro-pyran-4-yl)-nicotinamide

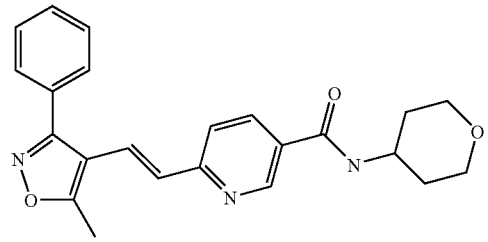 [SMILES: Cc1onc(-c2ccccc2)c1/C=C/c1ccc(C(=O)NC2CCOCC2)cn1]

As described in example 2, 6-[(E)-2-(5-methyl-3-phenyl-isoxazol-4-yl)-vinyl]-nicotinic acid methyl ester (200 mg, 0.62 mmol) instead of 6-[(E)-2-(5-methyl-3-phenyl-isoxazol-4-yl)-vinyl]-nicotinic acid methyl ester, and 4-aminotetrahydropyran instead of isopropylamine, was converted to the title compound (188 mg, 77%) which was obtained as a white solid after purification by chromatography (silica, dichloromethane:methanol 100:0 to 95:5). MS: m/e=390.4 [M+H]$^+$.

Example 4

N-(2-Hydroxy-ethyl)-6-[(E)-2-(5-methyl-3-phenyl-isoxazol-4-yl)-vinyl]-nicotinamide

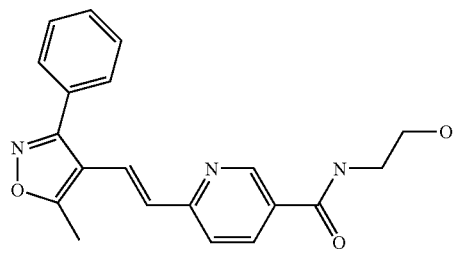 [SMILES: Cc1onc(-c2ccccc2)c1/C=C/c1ccc(C(=O)NCCO)cn1]

To a stirred solution of 6-[(E)-2-(5-methyl-3-phenyl-isoxazol-4-yl)-vinyl]-nicotinic acid methyl ester (200 mg, 0.62 mmol) in toluene (0.5 mL) was added ethanolamine (46 mg, 0.75 mmol) and TBD (26 mg, 0.10 mmol), then the reaction mixture was warmed to 35° C. After 3 h the reaction mixture was concentrated. Purification by chromatography (silica, dichloromethane:methanol 100:0 to 93:7) afforded the title compound (155 mg, 71%) as a white solid after trituration with hexane/ethyl acetate. MS: m/e=350.4 [M+H]$^+$.

Example 5

N-(2-Hydroxy-1-methyl-ethyl)-6-[(E)-2-(5-methyl-3-phenyl-isoxazol-4-yl)-vinyl]-nicotinamide

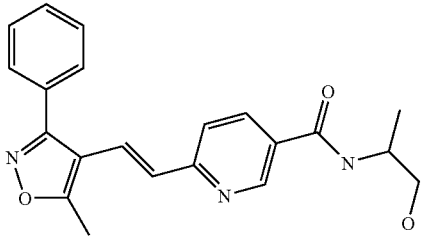 [SMILES: Cc1onc(-c2ccccc2)c1/C=C/c1ccc(C(=O)NC(C)CO)cn1]

As described in example 4, 6-[(E)-2-(5-methyl-3-phenyl-isoxazol-4-yl)-vinyl]-nicotinic acid methyl ester (200 mg, 0.62 mmol), using DL-2-amino-1-propanol instead of ethanolamine, was converted to the title compound (170 mg, 75%) which was obtained as a white solid after purification by chromatography (silica, dichloromethane:methanol 100:0 to 93:7). MS: m/e=364.4 [M+H]+.

Example 6

6-[(E)-2-(5-Methyl-3-phenyl-isoxazol-4-yl)-vinyl]-nicotinic acid

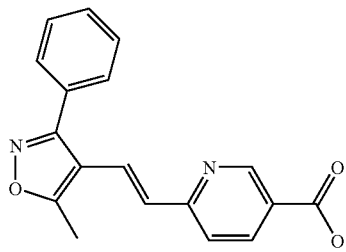 [SMILES: Cc1onc(-c2ccccc2)c1/C=C/c1ccc(C(=O)O)cn1]

To a suspension of 6-[(E)-2-(5-methyl-3-phenyl-isoxazol-4-yl)-vinyl]-nicotinic acid methyl ester (150 mg, 0.47 mmol) in THF (1.5 mL) and methanol (0.5 mL) was added a solution of lithium hydroxide monohydrate (39.2 mg, 0.94 mmol) in water (1.5 mL) added and the resulting mixture stirred at room temperature for 1 h. The mixture was acidified to pH 4 with HCl (1 N) and cooled to 0° C. The precipitate was filtered off and dried to afford the title compound (134 mg, 93%) which was obtained as a white solid. MS: m/e=305.4 [M–H]+.

Example 7

6-[(E)-2-(3-Butyl-5-methyl-isoxazol-4-yl)-vinyl]nicotinic acid methyl ester

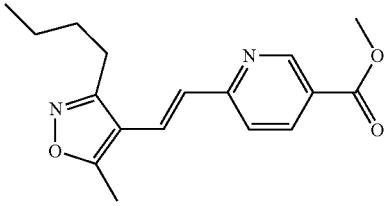 [SMILES: CCCCc1noc(C)c1/C=C/c1ccc(C(=O)OC)cn1]

a) 3-Butyl-5-methyl-isoxazole-4-carboxylic acid ethyl ester

To a suspension of N-chlorosuccinimide (16.1 g, 121 mmol) in chloroform (250 mL) at room temperature was added pyridine (0.95 g, 12.0 mmol) then a solution of pentanal oxime (12.2 g, 121 mmol) in chloroform (250 mL) was added dropwise over 20 min. The reaction mixture was stirred at 50° C. for 2 h then cooled to room temperature and a solution of ethyl (E)-3-(1-pyrrolidino)-2-butenoate (22.1 g, 121 mmol) in chloroform (120 mL) added dropwise. The reaction mixture was warmed to 50° C. and a solution of triethylamine (12.2 g, 121 mmol) in chloroform (120 mL) added dropwise. After 15 h the reaction mixture was cooled and extracted with water then citric acid (10% w/w aqueous solution). The combined aqueous phases were extracted with dichloromethane, then the combined organic phases were dried, filtered and concentrated. Purification by chromatography (silica, heptane:ethyl acetate=100:0 to 9:1) afforded the title compound (10.9 g, 43%) as a pale yellow liquid. MS: m/e=232.2 [M+H]+.

b) (3-Butyl-5-methyl-isoxazol-4-yl)-methanol

To a stirred solution of 3-butyl-5-methyl-isoxazole-4-carboxylic acid ethyl ester (9.8 g, 46.3 mmol) in THF (100 mL) under argon and at 0° C. was added lithium aluminium hydride (2.03 g, 53.4 mmol) in five portions. After 1 h the reaction mixture was quenched dropwise with Seignette salt solution. The reaction mixture was filtered and the filtrate extracted with ethyl acetate. The combined organic extracts were washed with Seignette salt solution then dried, filtered and concentrated. Purification by chromatography (silica, heptane:ethyl acetate=100:0 to 4:6) afforded the title compound (7.5 g, 95%) as a yellow liquid. MS: m/e=170.3 [M+H]+.

c) 3-Butyl-5-methyl-isoxazole-4-carbaldehyde

To a stirred solution of PCC (4.96 g, 23 mmol) and anhydrous magnesium sulfate (7.40 g, 61 mmol) in DCM (60 mL) was added a solution of (3-butyl-5-methyl-isoxazol-4-yl)-methanol (2.6 g, 15 mmol) in DCM (60 mL) at room temperature and under argon. After 3 h the reaction mixture was diluted with ether (100 mL) and filtered through a bed of silica and the filtrate was concentrated. Purification by chromatography (silica heptane:ethyl acetate=100:0 to 1:1) afforded the title compound (2.15 g, 84%) as a colorless liquid. MS: m/e=170.3 [M+H]+.

d) 6-[(E)-2-(3-Butyl-5-methyl-isoxazol-4-yl)-vinyl]-nicotinic acid methyl ester

As described in 1b, 3-butyl-5-methyl-isoxazole-4-carbaldehyde (1.0 g, 6.0 mmol) instead of 5-methyl-3-phenyl-4-isoxazolecarbaldehyde, was converted to the title compound (760 mg, 43%) which was obtained as a light brown solid after purification by chromatography (silica, dichloromethane:methanol 100:0 to 97.5:2.5). MS: m/e=170.3 [M+H]+.

Example 8

6-[(E)-2-(3-Butyl-5-methyl-isoxazol-4-yl)-vinyl]-N-isopropyl-nicotinamide

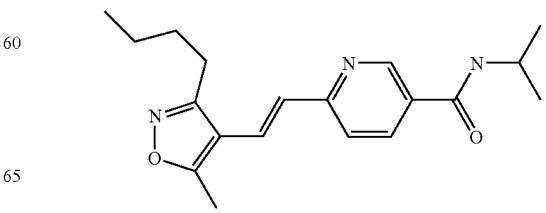

As described in example 2, 6-[(E)-2-(3-butyl-5-methyl-isoxazol-4-yl)-vinyl]-nicotinic acid methyl ester (80 mg, 0.21 mmol) instead of 6-[2-(5-methyl-3-phenyl-isoxazol-4-yl)-ethyl]-nicotinic acid methyl ester, was converted to the title compound (44 mg, 63%) which was obtained as a light yellow oil after purification by chromatography (silica, dichloromethane:methanol 100:0 to 95:5). MS: m/e=328.4 [M+H]$^+$.

Example 9

6-[(E)-2-(3-Butyl-5-methyl-isoxazol-4-yl)-vinyl]-N-(tetrahydro-furan-3-yl)-nicotinamide

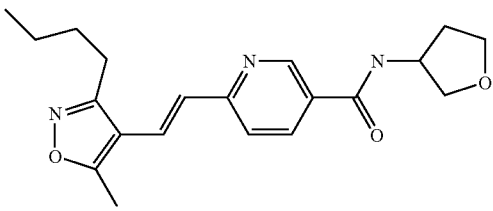 [SMILES: CCCCc1noc(C)c1/C=C/c1ccc(C(=O)NC2CCOC2)cn1]

As described in example 8, 6-[(E)-2-(3-butyl-5-methyl-isoxazol-4-yl)-vinyl]-nicotinic acid methyl ester (200 mg, 0.57 mmol), and tetrahydrofuran-3-amine instead of isopropylamine, was converted to the title compound (140 mg, 70%) which was obtained as a light red solid after purification by chromatography (silica, dichloromethane:methanol 100:0 to 94:6). MS: m/e=328.4 [M+H]$^+$.

Example 10

6-[(E)-2-(3-Butyl-5-methyl-isoxazol-4-yl)-vinyl]-N-(2-hydroxy-1-methyl-ethyl)-nicotinamide

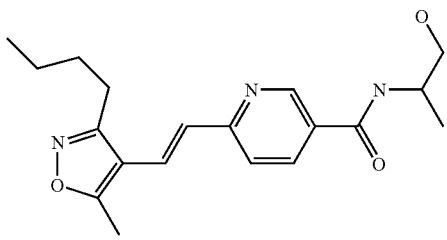 [SMILES: CCCCc1noc(C)c1/C=C/c1ccc(C(=O)NC(C)CO)cn1]

As described in example 4, 6-[(E)-2-(3-butyl-5-methyl-isoxazol-4-yl)-vinyl]-nicotinic acid methyl ester (100 mg, 0.28 mmol) instead of 6-[2-(5-methyl-3-phenyl-isoxazol-4-yl)-ethyl]-nicotinic acid methyl ester, and DL-2-amino-1-propanol instead of ethanolamine, was converted to the title compound (85 mg, 87%) which was obtained as a light yellow oil after purification by chromatography (silica, dichloromethane:methanol 100:0 to 94:6). MS: m/e=364.4 [M+H]$^+$.

Example 11

6-[(E)-2-(3-Butyl-5-methyl-isoxazol-4-yl)-vinyl]-N-(2-hydroxy-2-methyl-propyl)-nicotinamide

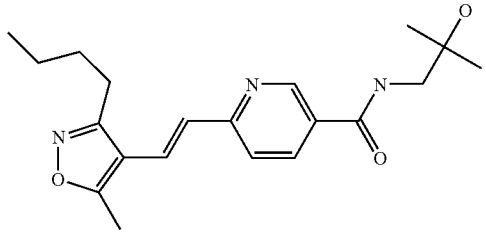 [SMILES: CCCCc1noc(C)c1/C=C/c1ccc(C(=O)NCC(C)(C)O)cn1]

As described in example 10, 6-[(E)-2-(3-butyl-5-methyl-isoxazol-4-yl)-vinyl]-nicotinic acid methyl ester (100 mg, 0.28 mmol), and 1-amino-2-methyl-propan-2-ol instead of DL-2-amino-1-propanol, was converted to the title compound (7.5 mg, 7%) which was obtained as a colorless solid after purification by chromatography (silica, dichloromethane:methanol 100:0 to 94:6). MS: m/e=364.4 [M+H]$^+$.

Example 12

6-[(E)-2-(3-Butyl-5-methyl-isoxazol-4-yl)-vinyl]-N-(tetrahydro-pyran-4-yl)-nicotinamide

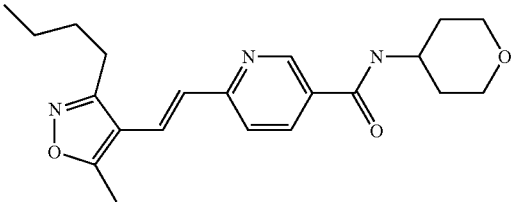 [SMILES: CCCCc1noc(C)c1/C=C/c1ccc(C(=O)NC2CCOCC2)cn1]

As described in example 9, 6-[(E)-2-(3-butyl-5-methyl-isoxazol-4-yl)-vinyl]-nicotinic acid methyl ester (100 mg, 0.28 mmol), and 4-aminotetrahydropyran instead of tetrahydrofuran-3-amine, was converted to the title compound (56 mg, 46%) which was obtained as a white solid after purification by chromatography (silica, dichloromethane:methanol 100:0 to 96.5:3.5) and trituration with isopropyl ether. MS: m/e=328.4 [M+H]$^+$.

Example 13

6-[(E)-2-(3-Butyl-5-methyl-isoxazol-4-yl)-vinyl]-N—((R)-2-hydroxy-1-methyl-ethyl)-nicotinamide

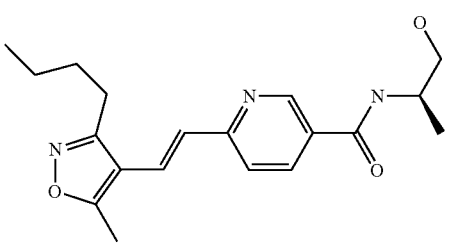 [SMILES: CCCCc1noc(C)c1/C=C/c1ccc(C(=O)N[C@H](C)CO)cn1]

As described in example 10, 6-[(E)-2-(3-butyl-5-methyl-isoxazol-4-yl)-vinyl]-nicotinic acid methyl ester (100 mg, 0.28 mmol), and D-2-amino-1-propanol instead of DL-2-amino-1-propanol, was converted to the title compound (36 mg, 31%) which was obtained as a colorless oil after purification by chromatography (silica, dichloromethane:methanol 100:0 to 96.5:3.5). MS: m/e=364.4 [M+H]$^+$.

Example 14

6-[(E)-2-(3-Butyl-5-methyl-isoxazol-4-yl)-vinyl]-N—((S)-2-hydroxy-1-methyl-ethyl)-nicotinamide

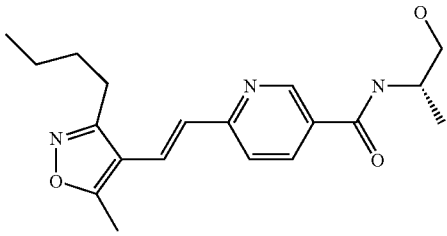 [SMILES: CCCCc1noc(C)c1/C=C/c1ccc(C(=O)N[C@@H](C)CO)cn1]

As described in example 10, 6-[(E)-2-(3-butyl-5-methyl-isoxazol-4-yl)-vinyl]-nicotinic acid methyl ester (100 mg, 0.28 mmol), and L-2-amino-1-propanol instead of DL-2-amino-1-propanol, was converted to the title compound (41 mg, 36%) which was obtained as a colorless oil after purification by chromatography (silica, dichloromethane:methanol 100:0 to 96.5:3.5). MS: m/e=364.4 [M+H]$^+$.

Example 15

6-[(E)-2-(3-Butyl-5-methyl-isoxazol-4-yl)-vinyl]-N-(2-hydroxy-1-hydroxymethyl-ethyl)-nicotinamide

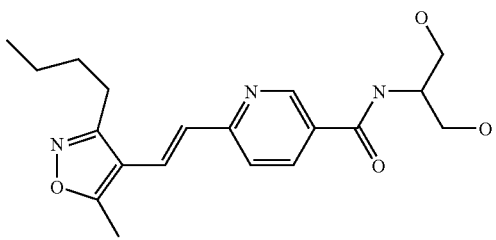 [SMILES: CCCCc1noc(C)c1/C=C/c1ccc(C(=O)NC(CO)CO)cn1]

As described in example 10, 6-[(E)-2-(3-butyl-5-methyl-isoxazol-4-yl)-vinyl]-nicotinic acid methyl ester (150 mg, 0.50 mmol), and 2-amino-1,3-propanol instead of DL-2-amino-1-propanol, was converted to the title compound (26 mg, 14%) which was obtained as a yellow solid after purification by chromatography (silica, dichloromethane:methanol 100:0 to 95:5). MS: m/e=364.4 [M+H]$^+$.

Example 16

N-Isopropyl-6-[2-(5-methyl-3-phenyl-isoxazol-4-yl)-ethyl]-nicotinamide

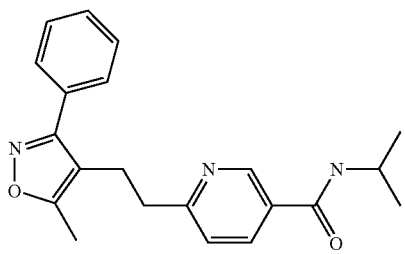 [SMILES: Cc1onc(-c2ccccc2)c1CCc1ccc(C(=O)NC(C)C)cn1]

a) 6-[2-(5-Methyl-3-phenyl-isoxazol-4-yl)-ethyl]-nicotinic acid n-Butyllithium solution was added dropwise to a stirred suspension of 6-methylnicotinic acid (137 mg, 1.0 mmol) in THF (3 mL) over 30 min at −74° C. After 1 h a solution of 4-chloromethyl-5-methyl-3-phenyl-isoxazole (208 mg, 1.0 mmol) in THF (3 mL) was added dropwise such that the temperature did not exceed −68° C. The reaction mixture was stirred at −74° C. for 1 h, then HCl (1 N, 10 mL) added and the reaction mixture warmed to room temperature and extracted with ethyl acetate. The combined organic extracts were dried, filtered and concentrated. Purification by chromatography (silica, heptane:ethyl acetate=100:0 to 9:1) afforded the title compound (20 mg, 6%) as a light yellow oil. MS: m/e=168.3 [M+H]$^+$.

b) N-Isopropyl-6-[2-(5-methyl-3-phenyl-isoxazol-4-yl)-ethyl]-nicotinamide

A solution of trimethyl aluminium (2 M in toluene, 0.32 mL, 0.65 mmol) was added dropwise to a solution of isopropylamine (38 mg, 0.65 mmol) in dioxane (1.5 mL) under argon and at room temperature. After 1 h a solution of 6-[2-(5-methyl-3-phenyl-isoxazol-4-yl)-ethyl]-nicotinic acid (50 mg, 0.16 mmol) in dioxane (1.5 mL) was added and the reaction mixture warmed to 90° C. After 15 h, the reaction mixture was cooled and carefully diluted with Seignette salt solution (0.5 mL). The mixture was filtered, the filter cake washed with dichloromethane, then the combined filtrates were concentrated. Purification by chromatography (silica, dichloromethane:methanol 100:0 to 96:4) afforded the title compound (45 mg, 79%) as a light yellow oil. MS: m/e=350.5 [M+H]$^+$.

Example 17

6-[2-(3-Butyl-5-methyl-isoxazol-4-yl)-ethyl]-N-(2-hydroxy-1-methyl-ethyl)-nicotinamide

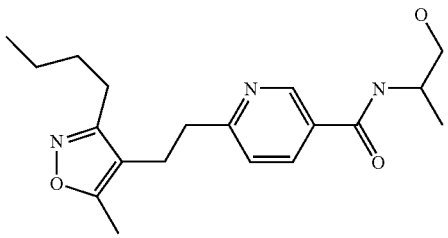 [SMILES: CCCCc1noc(C)c1CCc1ccc(C(=O)NC(C)CO)cn1]

A stirred mixture of 6-[(E)-2-(3-butyl-5-methyl-isoxazol-4-yl)-vinyl]-N-(2-hydroxy-1-methyl-ethyl)-nicotinamide (example 10, 32 mg, 0.093 mmol) and 10% Palladium on charcoal (5 mg) in ethanol (5 mL) was shaken under an atmosphere of hydrogen for 2 h. The reaction mixture was filtered and concentrated. Purification by chromatography (silica, dichloromethane:methanol 100:0 to 9:1) afforded the title compound (20 mg, 63%) as a colorless oil. MS: m/e=364.4 [M+H]$^+$.

Example 18

6-[2-(3-Butyl-5-methyl-isoxazol-4-yl)-ethyl]-N-(tetrahydro-furan-3-yl)-nicotinamide

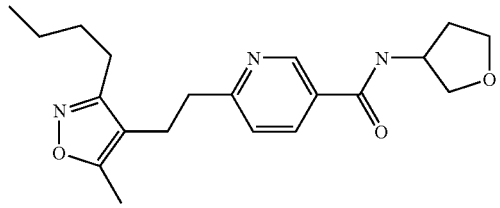

A stirred mixture of 6-[(E)-2-(3-butyl-5-methyl-isoxazol-4-yl)-vinyl]-N-(tetrahydro-furan-3-yl)-nicotinamide (31 mg, 0.087 mmol) and 10% Palladium on charcoal (5 mg) in ethanol (5 mL) was shaken under an atmosphere of hydrogen for 3 h. The reaction mixture was filtered and concentrated. Purification by chromatography (silica, dichloromethane:methanol 100:0 to 9:1) afforded the title compound (17 mg, 55%) as a colorless oil. MS: m/e=328.4 [M+H]+.

The invention claimed is:

1. A compound of formula I

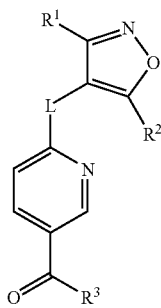

wherein
L is —CH$_2$—CH$_2$— or —CH=CH—;
R$^1$ is lower-alkyl or aryl,
wherein lower-alkyl is optionally substituted with 1-4 substituents independently selected from the group consisting of fluoro, cyano, hydroxy, lower-alkoxy and fluoro-lower-alkoxy,
and wherein aryl is optionally substituted with 1-4 substituents independently selected from the group consisting of halogen, cyano, hydroxy, lower-alkyl, fluoro-lower-alkyl, cyano-lower-alkyl, hydroxy-lower-alkyl, lower-alkyl-C(O)OH, lower-alkyl-C(O)O-lower-alkyl, lower-alkyl-CO—NH$_2$, lower-alkyl-CO—N(H, lower-alkyl), lower-alkyl-CO—N(lower-alkyl)$_2$, lower-alkyl-N(H, lower-alkyl), lower-alkyl-N(lower-alkyl)$_2$, lower-alkoxy-lower-alkyl, CO-lower-alkyl, COOH, COO-lower-alkyl, CONH$_2$, CON(H, lower-alkyl), CON(lower-alkyl)$_2$, NH$_2$, N(H, lower-alkyl), N(lower-alkyl)$_2$, lower-alkoxy, fluoro-lower-alkoxy, SO$_2$-lower-alkyl, SO$_2$—NH$_2$, SO$_2$—N(H, lower-alkyl), SO$_2$—N(lower-alkyl)$_2$, cycloalkyl, phenyloxy and phenyl;
R$^2$ is lower-alkyl optionally substituted with 1-4 substituents independently selected from the group consisting of fluoro, cyano, hydroxy, lower-alkoxy and fluoro-lower-alkoxy;
R$^3$ is —O—R$^4$ or N(R$^5$,R$^6$);
R$^4$ is hydrogen or lower-alkyl;
R$^5$ is hydrogen or lower-alkyl; and
R$^6$ is lower-alkyl or hydroxy-lower-alkyl,
or a pharmaceutically acceptable salt thereof.

2. The compound of claim 1, wherein L is —CH=CH—.
3. The compound of claim 1, wherein L is —CH$_2$—CH$_2$—.
4. The compound of claim 1, wherein R$^1$ is aryl or lower-alkyl.
5. The compound of claim 4, wherein R$^1$ is lower-alkyl.
6. The compound of claim 5, wherein R$^1$ is n-butyl.
7. The compound of claim 1, wherein R$^2$ is lower-alkyl.
8. The compound of claim 7, wherein R$^2$ is methyl.
9. The compound of claim 1, wherein R$^3$ is NR$^5$R$^6$.
10. The compound of claim 1, wherein R$^4$ is hydrogen or methyl.
11. The compound of claim 1, wherein R$^5$ is hydrogen.
12. The compound of claim 1, wherein R$^6$ is lower-alkyl.
13. The compound of claim 1, wherein R$^6$ is hydroxy-lower-alkyl.
14. The compound of claim 13, wherein R$^6$ is 2-hydroxy-1-methyl-ethyl.
15. The compound of claim 1, wherein the compound is selected from the group consisting of:

6-[(E)-2-(5-Methyl-3-phenyl-isoxazol-4-yl)-vinyl]-nicotinic acid methyl ester,
N-Isopropyl-6-[(E)-2-(5-methyl-3-phenyl-isoxazol-4-yl)-vinyl]-nicotinamide,
N-(2-Hydroxy-ethyl)-6-[(E)-2-(5-methyl-3-phenyl-isoxazol-4-yl)-vinyl]-nicotinamide,
N-(2-Hydroxy-1-methyl-ethyl)-6-[(E)-2-(5-methyl-3-phenyl-isoxazol-4-yl)-vinyl]-nicotinamide,
6-[(E)-2-(5-Methyl-3-phenyl-isoxazol-4-yl)-vinyl]-nicotinic acid,
6-[(E)-2-(3-Butyl-5-methyl-isoxazol-4-yl)-vinyl]-nicotinic acid methyl ester, and
6-[(E)-2-(3-Butyl-5-methyl-isoxazol-4-yl)-vinyl]-N-isopropyl-nicotinamide,
or a pharmaceutically acceptable salt thereof.

16. The compound of claim 1, wherein the compound is selected from the group consisting of
6-[(E)-2-(3-Butyl-5-methyl-isoxazol-4-yl)-vinyl]-N-(2-hydroxy-1-methyl-ethyl)-nicotinamide,
6-[(E)-2-(3-Butyl-5-methyl-isoxazol-4-yl)-vinyl]-N-(2-hydroxy-2-methyl-propyl)-nicotinamide,
6-[(E)-2-(3-Butyl-5-methyl-isoxazol-4-yl)-vinyl]-N—((R)-2-hydroxy-1-methyl-ethyl)-nicotinamide,
6-[(E)-2-(3-Butyl-5-methyl-isoxazol-4-yl)-vinyl]-N—((S)-2-hydroxy-1-methyl-ethyl)-nicotinamide,
6-[(E)-2-(3-Butyl-5-methyl-isoxazol-4-yl)-vinyl]-N-(2-hydroxy-1-hydroxymethyl-ethyl)-nicotinamide,
N-Isopropyl-6-[2-(5-methyl-3-phenyl-isoxazol-4-yl)-ethyl]-nicotinamide,
6-[2-(3-Butyl-5-methyl-isoxazol-4-yl)-ethyl]-N-(2-hydroxy-1-methyl-ethyl)-nicotinamide, and,
or a pharmaceutically acceptable salt thereof.

17. The compound of claim 1, wherein the compound is:
6-[(E)-2-(3-Butyl-5-methyl-isoxazol-4-yl)-vinyl]-N-(2-hydroxy-1-methyl-ethyl)-nicotinamide,
or a pharmaceutically acceptable salt thereof.

18. A pharmaceutical composition comprising a therapeutically effective amount of a compound of formula I

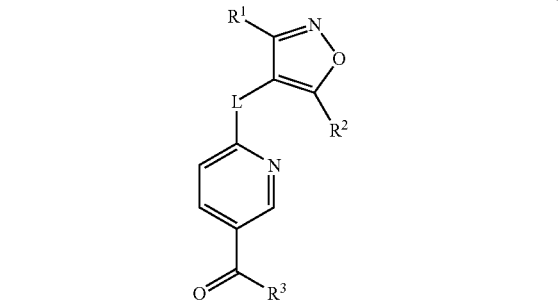

wherein
L is —CH$_2$—CH$_2$— or —CH=CH—;
R$^1$ is lower-alkyl or aryl,
wherein lower-alkyl is optionally substituted with 1-4 substituents independently selected from the group consisting of fluoro, cyano, hydroxy, lower-alkoxy and fluoro-lower-alkoxy,
and wherein aryl is optionally substituted with 1-4 substituents independently selected from the group consisting of halogen, cyano, hydroxy, lower-alkyl, fluoro-lower-alkyl, cyano-lower-alkyl, hydroxy-lower-alkyl, lower-alkyl-C(O)OH, lower-alkyl-C(O)O-lower-alkyl, lower-alkyl-CO—NH$_2$, lower-alkyl-CO—N(H, lower-alkyl), lower-alkyl-CO—N(lower-alkyl)$_2$, lower-alkyl-N(H, lower-alkyl), lower-alkyl-N(lower-alkyl)$_2$, lower-alkoxy-lower-alkyl, CO-lower-alkyl, COOH, COOlower-alkyl, $CONH_2$, $CON(H, lower-alkyl)$, $CON(lower-alkyl)_2$, $NH_2$, $N(H, lower-alkyl)$, $N(lower-alkyl)_2$, lower-alkoxy, fluoro-lower-alkoxy, $SO_2$-lower-alkyl, $SO_2-NH_2$, $SO_2-N(H, lower-alkyl)$, $SO_2-N(lower-alkyl)_2$, cycloalkyl, phenyloxy and phenyl;

$R^2$ is lower-alkyl optionally substituted with 1-4 substituents independently selected from the group consisting of fluoro, cyano, hydroxy, lower-alkoxy and fluoro-lower-alkoxy;

$R^3$ is $-O-R^4$ or $N(R^5,R^6)$;

$R^4$ is hydrogen or lower-alkyl;

$R^5$ is hydrogen or lower-alkyl; and $R^6$ is lower-alkyl or hydroxy-lower-alkyl, or a pharmaceutically acceptable salt thereof and a pharmaceutically acceptable carrier.

* * * * *